United States Patent [19]

Schacht et al.

[11] 4,072,754
[45] Feb. 7, 1978

[54] HYDRATROPIC ACID DERIVATIVES AND PROCESS FOR THE PRODUCTION THEREOF

[75] Inventors: Erich Schacht; Werner Mehrhof; Zdenek Simane; Herbert Nowak; Detlev Kayser, all of Darmstadt, Germany

[73] Assignee: Merck Patent Gesellschaft mit beschrankter Haftung, Darmstadt, Germany

[21] Appl. No.: 527,089

[22] Filed: Nov. 25, 1974

[30] Foreign Application Priority Data

Nov. 26, 1973 Germany .............................. 235878

[51] Int. Cl.² .................. C07C 65/14; C07C 69/76; A61K 31/19; A61K 31/235
[52] U.S. Cl. .................. 424/308; 260/287 T; 260/293.72; 260/313.1; 260/326.1; 260/453 AR; 260/520 C; 424/258; 424/267; 424/274; 424/317; 560/56; 560/59; 560/62; 560/63
[58] Field of Search .................. 260/473 G, 520 C; 424/308, 317

[56] References Cited

U.S. PATENT DOCUMENTS

| 3,517,051 | 6/1970 | Bolhofer | 260/520 C |
| 3,641,110 | 2/1972 | Beneze | 260/520 C |
| 3,707,549 | 12/1972 | Mills | 260/52 B |
| 3,755,603 | 8/1973 | Harrison et al. | 260/473 G |

FOREIGN PATENT DOCUMENTS

| 755,105 | 3/1967 | Canada. |
| 1,552,793 | 1/1969 | France. |

OTHER PUBLICATIONS

Yale, Journal of Medicinal & Pharmaceutical Chemistry, vol. 1 (2), 1959, p. 1.

*Primary Examiner*—Norman Morgenstern
*Attorney, Agent, or Firm*—Millen & White

[57] ABSTRACT

Hydratropic acid derivatives of the formula

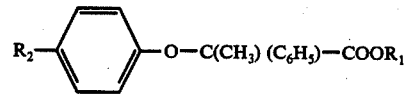

wherein $R_1$ is H, alkyl of 1-4 carbon atoms, 2-acetamidoethyl, 1-methyl-4-piperidyl, or 2,3-dihydroxypropyl, and $R_2$ is Hal, phenyl, 4-Hal-phenyl, 4-Hal-phenoxy, 4-Hal-phenoxymethyl, 1,2,3,4-tetrahydro-1-naphthyl, 1-pyrryl, piperidino, isoindolino, 1,2,3,4-tetrahydroquinolino, 1,2,3,4-tetrahydro-4-quinolyl or 1-methyl-1,2,3,4-tetrahydro-4-quinolyl, Hal being F, Cl, or Br, and the physiologically acceptable salts thereof, which possess cholesterol and triglyceride serum-level-lowering activity, can be prepared by reacting a phenol of the formula

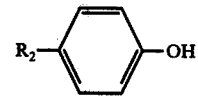

with a compound of the formula $X-C(CH_3)(C_6H_5)-COOR_1$ wherein X represents Cl, Br, I, OH, or esterified OH.

15 Claims, No Drawings

HYDRATROPIC ACID DERIVATIVES AND PROCESS FOR THE PRODUCTION THEREOF

BACKGROUND OF THE INVENTION

This invention relates to novel hydratropic acid derivatives.

SUMMARY OF THE INVENTION

In a composition aspect, this invention relates to novel hydratropic acid derivatives of the general Formula I

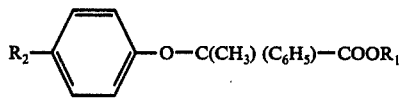      I wherein $R_1$ is H or $R_3$, $R_2$ is Hal, phenyl, 4-Hal-phenyl, 4-Hal-phenoxy, 4-Hal-phenoxymethyl, 1,2,3,4-tetrahydro-1-naphthyl, 1-pyrryl, piperidino, isoindolino, 1,2,3,4-tetrahydroquinolino, 1,2,3,4-tetrahydro-4-quinolyl, or 1-methyl-1,2,3,4-tetrahydro-4-quinolyl, $R_3$ is alkyl of 1-4 carbon atoms, 2-acetamidoethyl, 1-methyl-4-piperidyl, or 2,3-dihydroxypropyl, and Hal is F, Cl, or Br, and the physiologically acceptable salts thereof with acids and bases.

In another composition aspect, this invention relates to pharmaceutical compositions comprising a compound of this invention.

In a process aspect, this invention relates to processes for the production of the compounds of this invention.

DETAILED DISCUSSION

Compounds of Formula I and their physiologically acceptable salts possess, with good compatibility, excellent cholesterol serum level-lowering, and liver-enzyme-inducing activity.

Cholesterol-level-lowering activity can be determined, for example, in the rat serum according to the method by Levine et al. (Automation in Analytical Chemistry, Technicon Symposium 1967, Mediad, New York, pp. 25–28), and the triglyceride-level-lowering activity can be determined in accordance with the method by Noble and Campbell (Clin. Chem. 16 [1970], pp. 166–170).

The compounds of Formula I and the physiologically acceptable salts thereof can be employed as medicinal agents and also as intermediates for the production of other drugs.

In the compounds of Formula I, $R_1$ is preferably H and $R_3$ is preferably methyl, ethyl, 2-acetamidoethyl, 1-methyl-4-piperidyl, or 2,3-dihydroxypropyl. $R_3$ can also be n-propyl, isopropyl, n-butyl, isobutyl, sec.-butyl, and tert.-butyl. Hal is preferably Cl. Accordingly, among the compounds of Formula I wherein $R_2$ is a Hal atom or a group which contains a Hal atom, preferred are those wherein the Hal atom is chlorine, i.e., Cl, 4-chlorophenyl, 4-chlorophenoxy and 4-chlorophenoxymethyl. Thus, $R_2$ is preferably Cl, 4-chlorophenyl, 4-chlorophenoxy, 4-chlorophenoxymethyl, 1,2,3,4-tetrahydroquinolino, 1,2,3,4-tetrahydro-4-quinolyl, or 1-methyl-1,2,3,4-tetrahydro-4-quinolyl.

Especially preferred compounds of Formula I are those wherein at least one of $R_1$, $R_2$ and $R_3$ has one of the above preferred values.

Preferred groups of compounds which otherwise correspond to Formula I but wherein:

| | |
|---|---|
| Ia | $R_3$ is methyl, ethyl, 2-acetamidoethyl, 1-methyl-4-piperidyl, or 2,3-dihydroxypropyl; |
| Ib | $R_3$ is methyl or ethyl; |
| Ic | $R_2$ is Cl, 4-chlorophenyl, 4-chlorophenoxy, 4-chlorophenoxymethyl, 1,2,3,4-tetrahydroquinolino, 1,2,3,4-tetrahydro-4-quinolyl, or 1-methyl-1,2,3,4-tetrahydro-4-quinolyl; |
| Id | $R_2$ is 4-chlorophenoxy, 4-chlorophenoxymethyl, isoindolino, 1,2,3,4-tetrahydroquinolino, 1,2,3,4-tetrahydro-4-quinolyl, or 1-methyl-1,2,3,4-tetrahydro-4-quinolyl; |
| Ie | $R_3$ is methyl, ethyl, 2-acetamidoethyl, 1-methyl-4-piperidyl, or 2,3-dihydroxypropyl, and $R_2$ is 4-chlorophenoxy, 4-chlorophenoxymethyl, isoindolino, 1,2,3,4-tetrahydroquinolino, 1,2,3,4-tetrahydro-4-quinolyl, or 1-methyl-1,2,3,4-tetrahydro-4-quinolyl; |
| If | $R_2$ is 1-methyl-1,2,3,4-tetrahydro-4-quinolyl; |
| Ig | $R_1$ is H, especially those of Ic and Id. |

In its process aspect, this invention relates to a process for the preparation of compounds of Formula I, and the physiologically acceptable salts thereof, wherein a. a phenol of Formula II

      II is reacted with a compound of Formula III $$X-C(CH_3)(C_6H_5)-COOR_1 \quad \text{III}$$

wherein X is Cl, Br, I, OH, or esterified OH; or b. a compound of Formula IV

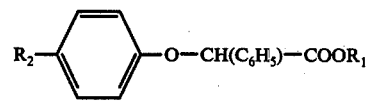      IV is treated with a methylating agent; or c. a compound of Formula V

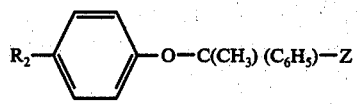      V wherein Z is a functionally modified carboxyl group differing from COOR$_1$, is treated with a solvolyzing agent.

Optionally, in a thus-obtained compound of Formula I, an $R_1$ group is converted into another $R_1$ group by treatment with an esterifying, interesterifying, or solvolyzing agent, and/or a thus-obtained compound of Formula I is converted, by treatment with an acid and/or base into a physiologically acceptable salt thereof, or a compound of Formula I is liberated from a salt thereof with a base or with an acid by treatment with an acid or base, respectively.

In Formulae II through V, $R_1$ and $R_2$ have the values given above for compounds of Formula I.

X is preferably Cl or Br but can also be, in addition to free OH and I, alkylsulfonyloxy, preferably of 1–6 carbon atoms (e.g., methanesulfonyloxy), arylsulfonyloxy of especially 6-10 carbon atoms (e.g., benzenesulfonyloxy, p-toluenesulfonyloxy, 1- or 2-naphthalenesulfonyloxy), or acyloxy, preferably of especially 1-7 carbon atoms (e.g., acetoxy or benzoyloxy).

The compounds of Formula I can be produced in accordance with conventional methods described in the literature.

Preferably, they are obtained by reacting a phenol II with a hydratropic acid derivative III. The phenol II is generally known. For example, see German Unexamined Laid-Open Application DOS 2,112,272. They can be prepared according to methods known per se, for example, by splitting the methyl ethers thereof, i.e., compounds otherwise corresponding to Formula II but having an $OCH_3$ group in place of OH, with HBr. The hydratropic acid derivatives III are known for the largest part. They also can be prepared according to methods disclosed in the literature. The phenol II can first be converted into a salt, especially into a metallic salt, e.g., an alkali metal salt, preferably a Li, Na, or K salt. For salt formation, the phenol can be reacted with a reagent which forms metallic salts, e.g., an alkali metal, e.g., Na, an alkali metal hydride or amide, e.g., LiH, NaH, $NaNH_2$ or $KNH_2$, a lower alkali metal alcoholate, e.g., lithium, sodium and potassium methylate, ethylate and tert.-butylate, an organometallic compound, e.g., as butyllithium, phenyllithium and phenylsodium, a metal hydroxide, carbonate, or bicarbonate, e.g., lithium, sodium, potassium, or calcium hydroxide, carbonate and bicarbonate. The phenolate is suitably prepared in the presence of a solvent, for example, a hydrocarbon, e.g., hexane, benzene, toluene, or xylene; an ether, e.g., diethyl ether, diisopropyl ether, tetrahydrofuran (THF), dioxane, or diethylene glycol dimethyl ether; an amide, e.g., dimethylformamide (DMF) or hexamethylphosphoric triamide (HMPA); an alcohol, e.g., methanol or ethanol; a ketone, e.g., acetone or butanone; or a mixture thereof. The phenol II and/or a salt thereof is reacted with compound III preferably in the presence of a diluent, e.g., the solvent utilized for the preparation of the salt but which can also be replaced by another solvent or can be diluted with such other solvent. The reaction occurs normally at temperatures of from $-20°$ to 150°, preferably 20° to 120°, particularly advantageously at the boiling temperature of the solvent. The reaction can be conducted under an inert gas, for example, nitrogen. The phenolate can also be formed in situ in which case, the phenol II and the compound III are allowed to react with each other in the presence of the saltforming reagent.

An especially preferred method resides in refluxing the compounds II and III (X = Cl or Br, $R_1 = CH_3$ or $C_2H_5$) together with an alcoholic, e.g., ethanolic, sodium alcoholate solution for 2-8 hours.

It is also possible to react a free phenol II with a hydroxy acid derivative of Formula III (X = OH), preferably in the presence of a condensation agent. Suitable condensation agents are, for example, acidic dehydration catalysts, e.g., mineral acids, including sulfuric acid or phosphoric acid, also p-toluenesulfonyl chloride, arsenic acid, boric acid, $NaHSO_4$ or $KHSO_4$, furthermore diaryl carbonates, e.g., diphenyl carbonate, dialkyl carbonates, e.g., dimethyl or diethyl carbonate, and carbodiimides, e.g., dicyclohexylcarbodiimide. If an acid is used as the condensation agent, the reaction is suitably effected in an excess of the acid without adding a further solvent, at temperatures of from about 0° to about 100°, preferably 50° to 60°. It is also possible to add diluents, e.g., benzene, toluene and dioxane. With a carbonic acid ester, the reaction is preferably conducted at a higher temperature, suitably from about 100° to about 210°, especially 180° to 200°. If desired, a transesterification catalyst, e.g., sodium or potassium carbonate or sodium methylate, can be employed in this case.

Hydratropic acid derivatives I can also be obtained by the methylation of corresponding phenylacetic acid derivatives IV. These phenylacetic acid derivatives are generally known; They can be obtained, for example, by reacting a phenol II with a compound of the formula $C_6H_5$—CHX—$COOR_1$ under the conditions indicated for the reaction of compounds II with compounds III.

Suitable methylating agents for the methylation IV are, for example, methyl chloride, bromide, iodide, p-toluenesulfonate, as well as dimethyl sulfate. Prior to the methylation, the compounds IV are suitably converted into a metal derivative thereof, for example, by reaction with an alcoholate, e.g., sodium ethylate or potassium tert.-butylate, a hydride, such as sodium hydride, an amide, e.g., sodium amide or lithium diisopropylamide, an organometallic compound, e.g., n-butyllithium, or a metal, e.g., sodium, e.g., in liquid ammonia. This conversion takes place advantageously in an inert solvent, e.g., an alcohol, for example, methanol, ethanol, or tert.-butanol, an ether, e.g., diethyl ether, an amide, e.g., DMF or HMPA, or a hydrocarbon, e.g., benzene, as well as mixtures of these solvents. The subsequent reaction with the methylating agent is suitably effected in the same reaction mixture. The reaction temperatures are normally about $-20°$ to $+120°$, preferably about 0° to 80°. The reaction times range preferably from about 1 hour to 48 hours.

The hydratropic acid derivatives I can also be obtained by solvolysis, preferably hydrolysis, of other hydratropic acid derivatives of Formula V.

In these compounds, Z especially is one of the following (wherein the groups R' and R" to be split off can be groups of any desired type and mean, for example, alkyl of preferably 1-4 carbon atoms, which can be identical or different and can also mean, collectively, for example, tetramethylene or pentamethylene, optionally interrupted by O): $CHal_3$; COOR''' (wherein R''' is a group different from $R_3$ and is, in particular, alkyl of 5-12 carbon atoms or an optionally substituted alkyl group which is, however, different from $R_3$); $C(OR')_3$; COOAcyl wherein Acyl is the residue of a carboxylic acid of up to 25 carbon atoms, preferably an acyl radical corresponding to the hydratropic acid (I), of the formula

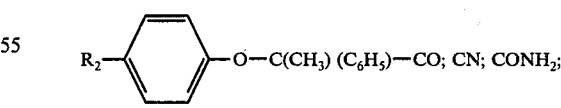

CONHR'; CONR'R"; CONHOH; C(OH)=NOH; $CONHNH_2$; $CON_3$; C(OR')=NH; $C(NH_2)=NNH_2$; $C(NHNH_2)=NH$; CSOH; COSH; CSOR'; $CSNH_2$; CSNHR'; or CSNR'R". Preferably, Z is a nitrile or acid amide group. The compounds V are obtainable, for example, by reacting the phenols II with compounds of the formula X—C($CH_3$) ($C_6H_5$)—Z in accordance with the methods described above.

A hydrolysis of compounds of Formula V can be accomplished in an acidic or alkaline medium at temperatures of about −20° to 300°, preferably at the boiling temperature of the selected solvent. Suitable acidic catalysts are, for example, hydrochloric, sulfuric, phosphoric, or hydrobromic acid. Advantageous basic catalysts are sodium, potassium, calcium hydroxide, sodium or potassium carbonate. Preferred solvents for the reaction are water, lower alcohols, e.g., methanol or ethanol, ethers, e.g., THF or dioxane, amides, e.g., DMF, nitriles, e.g., acetonitrile, sulfones, e.g., tetramethylenesulfone and mixtures of these solvents, especially water-containing mixtures. The preferred hydrolysis of nitriles (V, $Z = CN$) and acid amides (V, $Z = CONH_2$, $CONHR'$, or $CONR'R''$) is suitably conducted in an acidic medium, e.g., acetic acid/hydrochloric acid, or in an alkaline medium, e.g., alcoholic alkali.

With the aid of solvolytic methods, it is also possible to produce esters of Formula I ($R_1 = R_3$). For example, the nitriles V ($Z = CN$) can be converted by reaction with alcoholic hydrochloric acid into the corresponding imino alkyl ether hydrochlorides and these can be converted, by partial hydrolysis, into the corresponding alkyl esters.

If desired, the $R_1$ group, in a thus-obtained compound of Formula I, can be converted by esterification, transesterification, or solvolysis, into another $R_1$ group according to methods described in the literature.

It is possible, for example, to esterify a thus-produced acid of Formula I ($R_1 = H$) with the respective alcohol of the formula $R_3OH$, suitably in the presence of an inorganic or organic acid, e.g., HCl, HBr, HI, $H_2SO_4$, $H_3PO_4$, trifluoroacetic acid, benzenesulfonic acid, or p-toluenesulfonic acid, or an acidic ion exchanger, optionally in the presence of an inert solvent, e.g., benzene, toluene, or xylene, at temperatures of from 0° to preferably the boiling temperature. The alcohol is preferably used in excess. The esters can also be obtained by chemically adding the carboxylic acids I ($R_1 = H$) to olefins, e.g., isobutylene, or by reacting the carboxylic acids with diazoalkanes, e.g., diazomethane. Furthermore, the esters can be produced by reacting metallic salts of the acids I ($R_1 = H$), preferably the alkali metal, lead, or silver salts, with halogenides of the formula $R_3Hal$ or with corresponding chlorosulfites of the formula $R_3OSQCl$, wherein the thus-obtained adducts are thereafter thermally decomposed. The esterification can also be effected in several stages. For example, it is possible to first produce from the acid I ($R_1 = H$) the corresponding acid halogenide, e.g., the acid chloride, and then react the latter with the alcohol $R_3OH$, optionally in the presence of an acidic or basic catalyst.

Furthermore, the desired esters of Formula I ($R_1 = R_3$) can be obtained by transesterification, especially by reacting other esters with an excess of the respective alcohol, or by reacting the carboxylic acids I ($R_1 = H$) with any desired other ester of the respective alcohol, preferably an alkanoate wherein the alkanoyl group is of up to 4 carbon atoms, especially in the presence of a basic or acidic catalyst, e.g., sodium ethylate or sulfuric acid, and at temperatures of from 0° to preferably the boiling temperature.

It is also possible to convert the $R_1$ group of a thusobtained compound of Formula I into another $R_1$ group by treatment with a solvolyzing agent, especially to saponify a thusproduced ester of the Formula I ($R_1 = R_3$) to the corresponding acid I ($R_1 = H$). The solvolysis or saponification can be conducted according to one of the above-mentioned methods for the solvolysis of the compounds of Formula V. Preferably, the esters are saponified by treatment with an alcoholic alkali solution, e.g., ethanolic potassium hydroxide, at temperatures of from about 20° to 120°, preferably under boiling temperatures.

A basic compound of Formula I can be converted into the associated acid addition salt with the aid of an acid. Suitable are acids yielding physiologically acceptable salts. Thus, organic and inorganic acids can be used, e.g., aliphatic, alicyclic, araliphatic, aromatic, or heterocyclic mono- or polybasic carboxylic or sulfonic acids, such as formic acid, acetic acid, propionic acid, pivalic acid, diethylacetic acid, malonic acid, succinic acid, pimelic acid, fumaric acid, maleic acid, lactic acid, tartaric acid, malic acid, aminocarboxylic acids, sulfamic acid, benzoic acid, salicylic acid, phenylpropionic acid, citric acid, gluconic acid, ascorbic acid, nicotinic acid, isonicotinic acid, methanesulfonic acid, ethanedisulfonic acid, 2-hydroxyethanesulfonic acid, p-toluenesulfonic acid, naphthalene-mono- and -disulfonic acids, sulfuric acid, nitric acid, hydrohalic acids, such as hydrochloric acid or hydrobromic acid, or phosphoric acids, such as orthophosphoric acid.

The acids of Formula I ($R_1 = H$) can be converted into one of the physiologically acceptable metal and/or ammonium salts thereof by reaction with a base. Suitable salts are, in particular, the sodium, potassium, magnesium, calcium, and ammonium salts, as well as substituted ammonium salts, such as, for example, the dimethyl-, diethyl-, and diisopropylammonium, monoethanol-, diethanol-, and triethanolammonium, cyclohexylammonium, dicyclohexylammonium, and dibenzylethylenediammonium salts.

Conversely, compounds of Formula I can be liberated from their acid addition salts thereof by treatment with strong bases and/or from the metal and ammonium salts thereof by treatment with acids.

The compounds of Formula I can contain one or several centers of asymmetry and are ordinarily present in the racemic form. The racemates can be separated into their optical antipodes with the aid of conventional methods as indicated in the literature. Furthermore, it is, of course, possible to obtain optically active compounds according to the aforedescribed methods by employing starting materials which are already optically active.

The compounds of Formula I and/or optionally the physiologically acceptable salts thereof can be used in the human or veterinary medicine in a mixture with solid, liquid and/or semiliquid excipients. Suitable carrier substances are those organic or inorganic materials which are suitable for parenteral, enteral, or topical application and which do not react with the novel compounds, such as, for example, water, vegetable oils, benzyl alcohols, polyethylene glycols, gelatin, lactose, amylose, magnesium stearate, talc, vaseline, cholesterol. Suitable for parenteral application are especially solutions, preferably oily or aqueous solutions, as well as suspensions, emulsions, or implants. Suitable for enteral application are tablets, dragees, capsules, syrups, elixirs, or suppositories, and for topical administration ointments, creams, or powders. The above-mentioned preparations can optionally be sterilized or can contain auxiliary substances, such as lubricants, preservatives, stabilizers, or wetting agents, emulsifiers, salts for influencing the osmotic pressure, buffer substances, coloring agents, flavor-ameliorating agents and/or aromatic substances.

The compounds of Formula I and their salts are preferably utilized in dosages of from about 10 to 1,000 mg. per dosage unit. The daily dosage is preferably from about 0.2 to 20 mg./kg. of body weight. Oral administration is preferred.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. The temperatures are indicated herein as degrees Celsius.

EXAMPLE 1 a. A solution of 4.6 g. of sodium in 140 ml. of methanol is combined with 27.55 g. of 1-methyl-4-(4-hydroxyphenyl)-1,2,3,4-tetrahydroquinoline hydrochloride. The mixture is agitated for 30 minutes at 20°, and then 25.7 g. of 2-bromo-2-phenylpropionic acid ethyl ester is added dropwise thereto and the mixture is refluxed thereafter for 4 hours. After concentrating the mixture by evaporation, the residue is combined with water and extracted with chloroform. From the organic phase, the ethyl ester of 2-phenyl-2-[4-(1-methyl-1,2,3,4-tetrahydro-4-quinolyl)-phenoxy]-propionic acid is obtained as a yellow oil; $n_D^{20} = 1.5738$.

Analogously, with the use of the following starting compounds:
  4-fluorophenol
  4-chlorophenol
  4-bromophenol
  4-hydroxydiphenyl
  4'-fluoro-4-hydroxydiphenyl
  4'-chloro-4-hydroxydiphenyl
  4'-bromo-4-hydroxydiphenyl
  4'-fluoro-4-hydroxydiphenyl ether
  4'-chloro-4-hydroxydiphenyl ether
  4'-bromo-4-hydroxydiphenyl ether
  4-(4-fluorophenoxymethyl)-phenol
  4-(4-chlorophenoxymethyl)-phenol
  4-(4-bromophenoxymethyl)-phenol
  4-(1,2,3,4-tetrahydro-1-naphthyl)-phenol
  1-(4-hydroxyphenyl)-pyrrole
  1-(4-hydroxyphenyl)-piperidine
  2-(4-hydroxyphenyl)-isoindoline
  1-(4-hydroxyphenyl)-1,2,3,4-tetrahydroquinoline
  4-(4-hydroxyphenyl)-1,2,3,4-tetrahydroquinoline,
the following final compounds are produced by reaction with the ethyl ester of 2-bromo-2-phenylpropionic acid:
  the ethyl ester of each of the following acids:
  2-phenyl-2-(4-fluorophenoxy)-propionic acid
  2-phenyl-2-(4-chlorophenoxy)-propionic acid, $n_D^{20} = 1.5497$
  2-phenyl-2-(4-bromophenoxy)-propionic acid
  2-phenyl-2-(4-phenylphenoxy)-propionic acid, m.p. 88°-89° (ethyl ester)
  2-phenyl-2-[4-(4-fluorophenyl)-phenoxy]-propionic acid
  2-phenyl-2-[4-(4-chlorophenyl)-phenoxy]-propionic acid, m.p. of the ethyl ester 92°-93°
  2-phenyl-2-[4-(4-bromophenyl)-phenoxy]-propionic acid
  2-phenyl-2-[4-(4-fluorophenoxy)-phenoxy]-propionic acid
  2-phenyl-2-[4-(4-chlorophenoxy)-phenoxy]-propionic acid, $n_D^{20} = 1.5747$
  2-phenyl-2-[4-(4-bromophenoxy)-phenoxy]-propionic acid
  2-phenyl-2-[4-(4-fluorophenoxymethyl)-phenoxy]-propionic acid
  2-phenyl-2-[4-(4-chlorophenoxymethyl)-phenoxy]-propionic acid
  2-phenyl-2-[4-(4-bromophenoxymethyl)-phenoxy]-propionic acid
  2-phenyl-2-[4-(1,2,3,4-tetrahydro-1-naphthyl)-phenoxy]-propionic acid
  2-phenyl-2-[4-(1-pyrryl)-phenoxy]-propionic acid m.p. of the ethyl ester 66°-67°
  2-phenyl-2-(4-piperidinophenoxy)-propionic acid
  2-phenyl-2-(4-isoindolinophenoxy)-propionic acid m.p. of the ethyl ester 108°-110°
  2-phenyl-2-[4-(1,2,3,4-tetrahydroquinolino)-phenoxy]-propionic acid
  2-phenyl-2-[4-(1,2,3,4-tetrahydro-4-quinolyl)-phenoxy]-propionic acid, $n_D^{20} = 1.6127$.

b. 10 g. of the ethyl ester of 2-phenyl-2-[4-(1-methyl-1,2,3,4-tetrahydro-4-quinolyl)-phenoxy]-propionic acid is refluxed with 10 g. of KOH in 100 ml. of ethanol for 3 hours. The mixture is concentrated by evaporation combined with water, extracted with ether, and then hydrochloric acid is added to pH 5. The thus-obtained 2-phenyl-2-[4-(1-methyl-1,2,3,4-tetrahydro-4-quinolyl)-phenoxy]-propionic acid (called Ih hereinbelow) is filtered; m.p. 172°. Cyclohexylamine salt, m.p. 190°-192°. Sodium salt, m.p. 257°-260°.

Analogously, the following final products are obtained by saponifying the corresponding ethyl esters:
  2-phenyl-2-(4-fluorophenoxy)-propionic acid, cyclohexylamine salt, decomposition at 216°-218°
  2-phenyl-2-(4-chlorophenoxy)-propionic acid, m.p. 101°-102°
  2-phenyl-2-(4-bromophenoxy)-propionic acid
  2-phenyl-2-(4-phenylphenoxy)-propionic acid, m.p. 125°-127°
  2-phenyl-2-[4-(4-fluorophenyl)-phenoxy]-propionic acid
  2-phenyl-2-[4-(4-chlorophenyl)-phenoxy]-propionid acid, m.p. 127°
  2-phenyl-2-[4-(4-bromophenyl)-phenoxy]-propionic acid
  2-phenyl-2-[4-(4-fluorophenoxy)-phenoxy]-propionic acid
  2-phenyl-2-[4-(4-chlorophenoxy)-phenoxy]-propionic acid, m.p. 113°-115°
  2-phenyl-2-[4-(4-bromophenoxy)-phenoxy]-propionic acid
  2-phenyl-2-[4-(4-fluorophenoxymethyl)-phenoxy]-propionic acid
  2-phenyl-2-[4-(4-chlorophenoxymethyl)-phenoxy]-propionic acid
  2-phenyl-2-[4-(4-bromophenoxymethyl)-phenoxy]-propionic acid
  2-phenyl-2-[4-(1,2,3,4-tetrahydro-1-naphthyl)-phenoxy]-propionic acid, cyclohexylamine salt, m.p. 195°-197°
  2-phenyl-2-[4-(1-pyrryl)-phenoxy]-propionic acid, m.p. 130°-133°
  2-phenyl-2-(4-piperidinophenoxy)-propionic acid, m.p. 159°-161°; cyclohexylamine salt, m.p. 203°-205°
  2-phenyl-2-(4-isoindolinophenoxy)-propionic acid
  2-phenyl-2-[4-(1,2,3,4-tetrahydroquinolino)-phenoxy]-propionic acid, cyclohexylamine salt, m.p. 196°-198°

2-phenyl-2-[4-(1,2,3,4-tetrahydro-4-quinolyl)-phenoxy]-propionic acid, cyclohexylamine salt, m.p. 184°–185°; sodium salt, m.p. 240°–243°.

c. A mixture of 3.87 g. of the acid Ih, 1.1 ml. of thionyl chloride, and 50 ml. of benzene is refluxed for 2 hours. The mixture is then evaporated, the residue dissolved in 15 ml. of DMF, and this solution is introduced within one hour under ice cooling into a solution of 1.03 g. of N-(2-hydroxyethyl)-acetamide in a mixture of 11 ml. of DMF and 1.6 g. of pyridine. The mixture is agitated for 24 hours at 20°, then poured into ice water, extracted with ether, the ether phase washed with dilute hydrochloric acid, and dried. After evaporation, dissolution of the crude product in chloroform/ethyl acetate 24:1, and filtration over silica gel, the (2-acetamidoethyl) ester of 2-phenyl-2-[4-(1-methyl-1,2,3,4-tetrahydro-4-quinolyl)-phenoxy]-propionic acid is thus obtained.

Analogously, from the corresponding acids, the following final products are obtained:

the (2-acetamidoethyl) ester of each of the following acids:

2-phenyl-2-(4-fluorophenoxy)-propionic acid
2-phenyl-2-(4-chlorophenoxy)-propionic acid
2-phenyl-2-(4-bromophenoxy)-propionic acid
2-phenyl-2-(4-phenylphenoxy)-propionic acid
2-phenyl-2-[4-(4-fluorophenyl)-phenoxy]-propionic acid
2-phenyl-2-[4-(4-chlorophenyl)-phenoxy]-propionic acid
2-phenyl-2-[4-(4-bromophenyl)-phenoxy]-propionic acid
2-phenyl-2-[4-(4-fluorophenoxy)-phenoxy]-propionic acid
2-phenyl-2-[4-(4-chlorophenoxy)-phenoxy]-propionic acid, this ester being an oil, $n_D^{20}$ = 1.5638
2-phenyl-2-[4-(4-bromophenoxy)-phenoxy]-propionic acid
2-phenyl-2-[4-(4-fluorophenoxymethyl)-phenoxy]-propionic acid
2-phenyl-2-[4-(4-chlorophenoxymethyl)-phenoxy]-propionic acid
2-phenyl-2-[4-(4-bromophenoxymethyl)-phenoxy]-propionic acid
2-phenyl-2-[4-(1,2,3,4-tetrahydro-1-naphthyl)-phenoxy]-propionic acid
2-phenyl-2-[4-(1-pyrryl)-phenoxy]-propionic acid
2-phenyl-2-(4-piperidinophenoxy)-propionic acid
2-phenyl-2-(4-isoindolinophenoxy)-propionic acid
2-phenyl-2-[4-(1,2,3,4-tetrahydroquinolino)-phenoxy]-propionic acid
2-phenyl-2-[4-(1,2,3,4-tetrahydro-4-quinolyl)-phenoxy]-propionic acid.

d. A mixture of 3.87 g. of the acid Ih, 3 g. of 1-methyl-4-hydroxypiperidine, 2.3 g. of dicyclohexylcarbodiimide, and 35 ml. of absolute THF is allowed to stand overnight at 20°. The mixture is then filtered, the filtrate is combined with water and extracted with ethyl acetate. After drying and evaporation, the crude product is dissolved in chloroform and filtered over silica gel, thus obtaining the (1-methyl-4-piperidyl) ester of 2-phenyl-2-[4-(1-methyl-1,2,3,4-tetrahydro-4-quinolyl)-phenoxy]-propionic acid.

Analogously, the corresponding acids yield the following final products:

the (1-methyl-4-piperidyl) ester of each of the following acids:

2-phenyl-2-(4-fluorophenoxy)-propionic acid
2-phenyl-2-(4-chlorophenoxy)-propionic acid
2-phenyl-2-(4-bromophenoxy)-propionic acid
2-phenyl-2-(4-phenylphenoxy)-propionic acid
2-phenyl-2-[4-(4-fluorophenyl)-phenoxy]-propionic acid
2-phenyl-2-[4-(4-chlorophenyl)-phenoxy]-propionic acid
2-phenyl-2-[4-(4-bromophenyl)-phenoxy]-propionic acid
2-phenyl-2-[4-(4-fluorophenoxy)-phenoxy]-propionic acid
2-phenyl-2-[4-(4-chlorophenoxy)-phenoxy]-propionic acid, $n_D^{20}$ of the (1-methyl-4-piperidyl) ester: 1.5716
2-phenyl-2-[4-(4-bromophenoxy)-phenoxy]-propionic acid
2-phenyl-2-[4-(4-fluorophenoxymethyl)-phenoxy]-propionic acid
2-phenyl-2-[4-(4-chlorophenoxymethyl)-phenoxy]-propionic acid
2-phenyl-2-[4-(4-bromophenoxymethyl)-phenoxy]-propionic acid
2-phenyl-2-[4-(1,2,3,4-tetrahydro-1-naphthyl)-phenoxy]-propionic acid
2-phenyl-2-[4-(1-pyrryl)-phenoxy]-propionic acid
2-phenyl-2-(4-piperidinophenoxy)-propionic acid
2-phenyl-2-(4-isoindolinophenoxy)-propionic acid
2-phenyl-2-[4-(1,2,3,4-tetrahydroquinolino)-phenoxy]-propionic acid
2-phenyl-2-[4-(1,2,3,4-tetrahydro-4-quinolyl)-phenoxy]-propionic acid.

e. A solution is prepared from 0.23 g. of sodium and 25 ml. of ethanol; 3.87 g. of the acid Ih is added thereto, and then 30 ml. of HMPA is introduced into this reaction mixture. At a bath temperature of 130°, the ethanol is gradually removed by distillation. After the addition of 0.8 ml. of 3-chloropropanediol, the temperature is raised to 160° and maintained for 7 hours. The reaction mixture is then poured on ice water, extracted with ether, dried, and evaporated, thus obtaining the (2,3-dihydroxypropyl) ester of 2-phenyl-2-[4-(1-methyl-1,2,3,4-tetrahydro-4-quinolyl)-phenoxy]-propionic acid.

Analogously, the corresponding acids yield the (2,3-dihydroxypropyl) esters of each of the following acids:

2-phenyl-2-(4-fluorophenoxy)-propionic acid
2-phenyl-2-(4-chlorophenoxy)-propionic acid
2-phenyl-2-(4-bromophenoxy)-propionic acid
2-phenyl-2-(4-phenylphenoxy)-propionic acid
2-phenyl-2-[4-(4-fluorophenyl)-phenoxy]-propionic acid
2-phenyl-2-[4-(4-chlorophenyl)-phenoxy]-propionic acid
2-phenyl-2-[4-(4-bromophenyl)-phenoxy]-propionic acid
2-phenyl-2-[4-(4-fluorophenoxy)-phenoxy]-propionic acid
2-phenyl-2-[4-(4-chlorophenoxy)-phenoxy]-propionic acid
2-phenyl-2-[4-(4-bromophenoxy)-phenoxy]-propionic acid
2-phenyl-2-[4-(4-fluorophenoxymethyl)-phenoxy]-propionic acid
2-phenyl-2-[4-(4-chlorophenoxymethyl)-phenoxy]-propionic acid
2-phenyl-2-[4-(4-bromophenoxymethyl)-phenoxy]-propionic acid
2-phenyl-2-[4-(1,2,3,4-tetrahydro-1-naphthyl)-phenoxy]-propionic acid 2-phenyl-2-[4-(1-pyrryl)-phenoxy]-propionic acid
2-phenyl-2-(4-piperidinophenoxy)-propionic acid
2-phenyl-2-(4-isoindolinophenoxy)-propionic acid
2-phenyl-2-[4-(1,2,3,4-tetrahydroquinolino)-phenoxy]-propionic acid
2-phenyl-2-[4-(1,2,3,4-tetrahydro-4-quinolyl)-phenoxy]-propionic acid.

EXAMPLE 2

2.39 g. of 1-methyl-4-(4-hydroxyphenyl)-1,2,3,4-tetrahydroquinoline is added to a suspension of 0.24 g. of NaH in 20 ml. of dimethylacetamide. The mixture is agitated for one hour at 20°, and, after the addition of 2.6 g. of the ethyl ester of 2-bromo-2-phenylpropionic acid, maintained for 20 hours at 90°, cooled, combined with water, and extracted with ether. The ether solution is washed twice with dilute sodium hydroxide solution and evaporated after drying, thus obtaining the ethyl ester of Ih.

EXAMPLE 3

A mixture of 2.39 g. of 1-methyl-4-(4-hydroxyphenyl)-1,2,3,4-tetrahydroquinoline and 0.23 g. of sodium in 50 ml. of xylene is refluxed for 3 hours. The mixture is then allowed to cool to 20°; 2.57 g. of the ethyl ester of 2-bromo-2-phenylpropionic acid in 10 ml. of xylene is added thereto, the suspension is agitated under boiling for 6 hours, cooled, and 2 ml. of ethanol is added thereto. The inorganic precipitate is filtered off, the filtrate evaporated, the residue taken up in ether, the solution washed with $NaHCO_3$ solution and saturated NaCl solution, dried over $MgSO_4$, and concentrated by evaporation, thus obtaining the ethyl ester of Ih.

EXAMPLE 4

1.5 g. of sulfuric acid is added to a mixture of 2.39 g. of 1-methyl-4-(4-hydroxyphenyl)-1,2,3,4-tetrahydroquinoline and 1.94 g. of the ethyl ester of 2-hydroxy-2-phenylpropionic acid; the reaction mixture is stirred for 2 hours at 50°–60°. After cooling, the mixture is combined with water, dilute sodium hydroxide solution is added to pH 8, and the aqueous phase is extracted with ether. The reaction mixture is then dried and evaporated, thus obtaining the ethyl ester of Ih.

EXAMPLE 5

(a) 2.39 g. of 1-methyl-4-(4-hydroxyphenyl)-1,2,3,4-tetrahydroquinoline is dissolved in 20 ml. of acetone. Under agitation, 0.4 g. of NaOH is added thereto and then, under stirring and boiling, 2.29 g. of 2-bromo-2-phenylpropionic acid in 6 ml. of acetone is added dropwise to the reaction mixture. The latter is agitated for another hour at 56° and allowed to stand for 24 hours. The acetone is distilled off, the residue is dissolved in 100 ml. of water, the solution washed repeatedly with ether and acidified with HCl to pH 4. The thus-obtained product is the acid Ih.

(b) One gram of Ih is dissolved in 20 ml. of ether and combined dropwise with ethereal diazomethane solution until the yellow coloring is permanent. After evaporation, the methyl ester of Ih is obtained as an oil.

(c) One gram of Ih is dissolved in 40 ml. of saturated ethanolic hydrochloric acid; the mixture is allowed to stand for 12 hours at 20°, refluxed for 2 hours, and evaporated. The residue is dissolved in water, the aqueous solution is adjusted to pH 8 with dilute sodium hydroxide solution, and extracted with ethyl acetate. The mixture is then dried and evaporated, thus producing the ethyl ester of Ih.

EXAMPLE 6

A mixture of 0.78 g. of $NaNH_2$ and 3.73 g. of 2-phenyl-2-[4-(1-methyl-1,2,3,4-tetrahydro-4-quinolyl)-phenoxy]-acetic acid in 30 ml. of THF is gradually heated under agitation to 70°. The mixture is then cooled to 20°, 20 ml. of HMPA is added thereto, the mixture is cooled to 0° and, at 0°, 1.5 g. of methyl iodide is added dropwise thereto. Thereafter, the mixture is heated for 3 hours under agitation to 70°, concentrated by evaporation, and the acid Ih is obtained after the usual workingup step has been completed.

EXAMPLE 7

At $-40°$, 50 mg. of iron (III) nitrate and then, under agitation, 2.3 g. of Na are dissolved in 100 ml. of liquid ammonia. After two hours of agitation, 3.54 g. of 2-phenyl-2-[4-(1-methyl-1,2,3,4-tetrahydro-4-quinolyl)-phenoxy]-acetonitrile is added thereto, the mixture stirred for 30 minutes, and then 19.2 ml. of dimethyl sulfate is added dropwise within one hour. The mixture is further agitated overnight at $-35°$ and then combined dropwise with another 10 ml. of dimethyl sulfate. After the ammonia has been evaporated, the residue is combined with water and extracted with ether. The crude 2-phenyl-2-[4-(1-methyl-1,2,3,4-tetrahydro-4-quinolyl)-phenoxy]-propionitrile obtained after the evaporation of the ether is refluxed for 40 hours with 3 g. of KOH in 30 ml. of ethanol and 3 ml. of water. The mixture is concentrated by evaporation, mixed with water, extracted with ether, hydrochloric acid is added to pH 5, and the acid Ih is thus produced.

EXAMPLE 8

One gram of 2-phenyl-2-[4-(1-methyl-1,2,3,4-tetrahydro-4-quinolyl)-phenoxy]-propionitrile is refluxed for 2 hours under nitrogen with 6 ml. of acetic acid and 6 ml. of concentrated hydrochloric acid. The mixture is then evaporated, dissolved in dilute NaOH, extracted with ether, hydrochloric acid is added to pH 5, and the acid Ih is obtained in this way.

EXAMPLE 9

Three grams of 2-phenyl-2-[4-(1-methyl-1,2,3,4-tetrahydro-4-quinolyl)-phenoxy]-propionic acid amide (obtainable from 1-methyl-4-(4-hydroxyphenyl)-1,2,3,4-tetrahydroquinoline and 2-bromo-2-phenylpropionic acid amide) and 5 g. of KOH are refluxed in 100 ml. of ethanol for 3 hours under nitrogen. The mixture is then evaporated, combined with water, extracted with ether, and hydrochloric acid is added to pH 5, thus obtaining the acid Ih.

The following examples relate to pharmaceutical preparations containing effective agents of general Formula I and the physiologically acceptable salts thereof, respectively:

EXAMPLE A: Tablets

A mixture, consisting of 100 kg. of the cyclohexylamine salt of acid Ih, 400 kg. of lactose, 120 kg. of potato starch, 20 kg. of talc, and 10 kg. of magnesium stearate, is compressed into tablets in the usual manner, so that each tablet contains 100 mg. of the active ingredient.

EXAMPLE B: Dragees

Analogously to Example A, tablets are compressed which are then coated in the usual way with a layer consisting of sugar, corn starch, talc, and tragacanth.

Analogously, tablets and dragees can be obtained which contain one or several of the other effective agents of Formula I and/or the physiologically acceptable salts thereof.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A hydratropic acid derivative of the formula

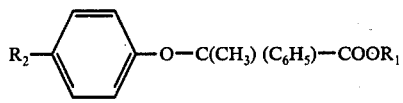

wherein $R_1$ is H, alkyl of 1-4 carbon atoms, 2-acetamidoethyl, or 2,3-dihydroxypropyl, and $R_2$ is Hal, phenyl, 4-Hal-phenyl, 4-Hal-phenoxy, 4-Hal-phenoxymethyl, 1,2,3,4-tetrahydro-1-naphthyl, Hal being F, Cl, or Br, or a physiologically acceptable salt thereof with an acid or base.

2. A compound of claim 1, wherein $R_1$ is H, alkyl of 1-4 carbon atoms, 2-acetamidoethyl, or 2,3-dihydroxypropyl.

3. A compound of claim 2 wherein $R_2$ is Hal, phenyl, 4-Hal-phenyl, 4-Hal-phenoxy, 4-Hal-phenoxymethyl or 1,2,3,4-tetrahydro-1-naphthyl.

4. A compound of claim 1, wherein $R_2$ is 4-chlorophenyl.

5. A compound of claim 1, wherein $R_2$ is 4-chlorophenoxy.

6. A compound of claim 1, wherein $R_2$ is Cl.

7. A compound of claim 1, wherein $R_2$ is phenyl.

8. A compound of claim 1, wherein $R_1$ is H.

9. A compound of claim 1, selected from the group consisting of 2-phenyl-2-(4-chlorophenoxy)-propionic acid, 2-phenyl-2-(4-phenylphenoxy)-propionic acid, 2-phenyl-2-(4-phenylphenoxy)-propionic acid ethyl ester, 2-phenyl-2-[4-(4-chlorophenyl)-phenoxy]-propionic acid, 2-phenyl-2-[4-(4-chlorophenoxy)-phenoxy]-propionic acid, 2-phenyl-2-[4-(4-chlorophenoxy)-phenoxy]-propionic acid (2-acetamidoethyl) ester, 2-phenyl-2-[4-(4-chlorophenoxymethyl)-phenoxy]-propionic acid, 2-phenyl-2-[4-(1,2,3,4-tetrahydro-1-naphthyl)-phenoxy]-propionic acid, and the physiologically acceptable salts thereof with an acid or a base.

10. A compound of claim 1 wherein $R_2$ is 4-chlorophenoxymethyl.

11. A compound of claim 1, 2-phenyl-2-(4-chlorophenoxy)propionic acid.

12. A compound of claim 1, 2-phenyl-2-[4-(4-chlorophenyl)-phenoxy]-propionic acid.

13. A compound of claim 1, 2-phenyl-2-(4-phenylphenoxy)-propionic acid.

14. A method of lowering from an abnormally high level at least one of cholesterol and triglyceride serum levels which comprises administering systemically to a patient with such abnormally high level an amount of a compound of claim 1 effective to lower substantially said level.

15. A pharmaceutical composition effective for lowering from an abnormally high level at least one of cholesterol and triglyceride serum levels comprising an amount of a compound of claim 1 per unit dosage effective to lower an abnormally high cholesterol or triglyceride serum level, in admixture with a pharmaceutically acceptable carrier.

* * * * *